United States Patent
Phipps et al.

(10) Patent No.: US 6,881,208 B1
(45) Date of Patent: Apr. 19, 2005

(54) METHOD AND DEVICE FOR TRANSDERMAL ELECTROTRANSPORT DELIVERY OF FENTANYL AND SUFENTANIL

(76) Inventors: Joseph B. Phipps, 14115 62nd. Place N., Maple Grove, MN (US) 55311; Mary Southam, 315 La Cuesta, Portola Valley, CA (US) 94025; Keith J. Bernstein, 29 Iroquis Trail, Somerville, NJ (US) 08876; Henk Noorduin, Augustalaan 45, Bergen op Zoom 4615 HM (NL)

(*) Notice: Subject to any disclaimer, the term of this patent is extended or adjusted under 35 U.S.C. 154(b) by 0 days.

(21) Appl. No.: 08/465,492

(22) Filed: Jun. 5, 1995

(51) Int. Cl.$^7$ ................................................ A61M 5/32
(52) U.S. Cl. ................................................ 604/501
(58) Field of Search ..................... 604/20–21, 890.1, 604/501; 607/115; 424/448–449

(56) References Cited

U.S. PATENT DOCUMENTS

| | | | |
|---|---|---|---|
| 4,141,359 A | 2/1979 | Jacobsen et al. | 128/172.1 |
| 4,588,580 A | 5/1986 | Gale et al. | 424/21 |
| 4,752,285 A | 6/1988 | Petelenz et al. | 604/20 |
| 4,931,046 A | * 6/1990 | Newman | |
| 5,006,108 A | 4/1991 | LaPrade | 604/20 |
| 5,047,007 A | 9/1991 | McNichols et al. | 604/20 |
| 5,135,477 A | 8/1992 | Untereker et al. | 604/20 |
| 5,135,479 A | 8/1992 | Sibalis et al. | 604/20 |
| 5,203,768 A | * 4/1993 | Haak et al. | |
| 5,224,927 A | 7/1993 | Tapper | 604/20 |
| 5,224,928 A | 7/1993 | Sibalis et al. | 604/20 |
| 5,232,448 A | 8/1993 | Zdeb | 604/153 |
| 5,246,418 A | 9/1993 | Haynes et al. | 604/20 |
| 5,254,081 A | 10/1993 | Maurer et al. | 604/20 |
| 5,298,017 A | 3/1994 | Theeuwes et al. | |
| 5,320,597 A | 6/1994 | Sage, Jr. et al. | 604/20 |
| 5,320,731 A | * 6/1994 | Muller et al. | 604/20 |
| 5,358,483 A | 10/1994 | Sibalis | 604/20 |

FOREIGN PATENT DOCUMENTS

| | | | |
|---|---|---|---|
| GB | 2239803 A | 7/1991 | A61N/1/30 |
| WO | WO90/03825 | 4/1990 | |
| WO | WO91/08795 | 6/1991 | |
| WO | WO93/01807 | 2/1993 | |

OTHER PUBLICATIONS

Sophie Thysman et al, *Anesthesia & Analgesia, In Vivo Iontophoresis of Fentanyl and Sufentanil in Rats: Pharmacokinetics and Acute Antinociceptive Effects*, vol. 77, No. 1, pp. 61–66, XP000576408, 1993.

(Continued)

*Primary Examiner*—Mark Bockelman

(57) ABSTRACT

The invention provides an improved electrotransport drug delivery system for analgesic drugs, namely fentanyl and sufentanil. The fentanyl/sufentanil is provided as a water soluble salt (eg, fentanyl hydrochloride) dispersed in a hydrogel formulation for use in an electrotransport device (10). In accordance with one aspect of the invention, the concentration of fentanyl/sufentanil in the donor reservoir (26) solution is above a predetermined minimum concentration, whereby the transdermal electrotransport flux of fentanyl/sufentanil is maintained independent of the concentration of fentanyl/sufentanil in solution. In accordance with a second aspect of the present invention, the donor reservoir (26) of the electrotransport delivery device (10) is comprised of silver and the donor reservoir (26) contains a predetermined "excess" loading of fentanyl/sufentanil halide to prevent silver ion migration with attendant skin discoloration. In accordance with a third aspect of the present invention, a transdermal electrotransport delivered dose of fentanyl/sufentanil is provided which is sufficient to induce analgesia in (eg, adult) human patients suffering from moderate-to-severe pain associated with major surgical procedures.

21 Claims, 4 Drawing Sheets

OTHER PUBLICATIONS

Thysman, Sophie, MSc, and Preat, Veronique, PhD, Anesth Analg 1993; 77:61–66, "In Vivo Iontophoresis of Fentanyl and Sufentanil in Rats: Pharmacokinetics and Actue Antinociceptive Effects".

Thysman, Sophie, T, Tasset, Chantal and Preat, Veronique, International Journal of Pharmaceutics, 101 (1994) 105–113, Elsevier Science Publishers B.V., "Transdermal Iontophoresis of Fentanyl: Delivery and Mechanistic Analysis".

Preat, Veronique and Thysman, Sophie, International Journal of Pharmaceutics, 96 (1993) 189–196, Elsevier Science Publishers B.V., "Trandermal Iontophoretic Delivery of Sufentanil".

Gourlay, Geoffrey K., et al., Pain, 37 (1989) 193–202, Elsevier Science Publishers B.V. (Biomedical Division), "The Transdermal Administration of Fentanyl in the Treatment of Postoperative Pain: Pharmacokinetics and Pharmacodynamic Effects".

Sebel, P.S., et al., European Journal of Clinical Pharmacology, (1987) 32: 529–531, "Transdermal Absorption of Fetanyl and Sufentanil in Man".

* cited by examiner

METHOD AND DEVICE FOR TRANSDERMAL ELECTROTRANSPORT DELIVERY OF FENTANYL AND SUFENTANIL

TECHNICAL FIELD

The invention relates generally to improved electrotransport drug delivery. Specifically, the invention relates to a device, composition and method for improved electrotransport delivery of analgesic drugs, particularly fentanyl and analogs of fentanyl. A composition is provided in the form of a hydrogel formulation for use in an electrotransport device.

BACKGROUND ART

The transdermal delivery of drugs, by diffusion through the epidermis, offers improvements over more traditional delivery methods, such as subcutaneous injections and oral delivery. Transdermal drug delivery avoids the hepatic first pass effect encountered with oral drug delivery. Transdermal drug delivery also eliminates patient discomfort associated with subcutaneous injections. In addition, transdermal delivery can provide more uniform concentrations of drug in the bloodstream of the patient over time due to the extended controlled delivery profiles of certain types of transdermal delivery devices. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focussed on reducing the physical resistance or enhancing the permeability of the skin for the delivery of drugs by passive diffusion. Various methods for increasing the rate of transdermal drug flux have been attempted, most notably using chemical flux enhancers.

Other approaches to increase the rates of transdermal drug delivery include use of alternative energy sources such as electrical energy and ultrasonic energy. Electrically assisted transdermal delivery is also referred to as electrotransport. The term "electrotransport" as used herein refers generally to the delivery of an agent (eg, a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field An agent can be delivered through the pores either passively (ie, without electrical assistance) or actively (ie, under the influence of an electric potential) However, in any given electrotransport process, more than one of these processes, including at least some "passive" diffusion, may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode, serves to close the electrical circuit through the body. For example, if the agent to be delivered is positively charged, ie, a cation, then the anode is the donor electrode, while the cathode is the counter electrode which serves to complete the circuit. Alternatively, if an agent is negatively charged, ie, an anion, the cathode is the donor electrode and the anode is the counter electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

To date, commercial transdermal electrotransport drug delivery devices (eg, the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a biocompatible electrolyte salt. The power supply unit has electrical controls for adjusting the amount of electrical current applied through the electrodes. The "satellite" electrodes are connected to the electrical power supply unit by long (eg, 1–2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al., U.S. Pat. No. 4,141,359 (see FIGS. 3 and 4); LaPrade, U.S. Pat. No. 5,006,108 (see FIG. 9); and Maurer et al., U.S. Pat. No. 5,254,081.

More recently, small self-contained electrotransport delivery devices have been proposed to be worn on the skin, sometimes unobtrusively under clothing, for extended periods of time. Such small self-contained electrotransport delivery devices are disclosed for example in Tapper, U.S. Pat. No. 5,224,927; Sibalis, et al., U.S. Pat. No. 5,224,928; and Haynes et al., U.S. Pat. No. 5,246,418.

There have recently been suggestions to utilize electrotransport devices having a reusable controller which is adapted for use with multiple drug-containing units. The drug-containing units are simply disconnected from the controller when the drug becomes depleted and a fresh drug-containing unit is thereafter connected to the controller. In this way, the relatively more expensive hardware components of the device (eg, batteries, LED's, circuit hardware, etc.) can be contained within the reusable controller, and the relatively less expensive donor reservoir and counter reservoir matrices can be contained in the single use/disposable drug-containing unit, thereby bringing down the overall cost of electrotransport drug delivery. Examples of electrotransport devices comprised of a reusable controller, removably connected to a drug-containing unit are disclosed in Sage, Jr. et al., U.S. Pat. No. 5,320,597; Sibalis, U.S. Pat. No. 5,358,483; Sibalis et al., U.S. Pat. No. 5,135,479 (FIG. 12); and Devane et al., UK Patent Application 2 239 803.

In further development of electrotransport devices, hydrogels have become particularly favored for use as the drug and electrolyte reservoir matrices, in part, due to the fact that water is the preferred liquid solvent for use in electrotransport drug delivery due to its excellent biocompatiblity compared with other liquid solvents such as alcohols and glycols. Hydrogels have a high equilibrium water content and can quickly absorb water. In addition, hydrogels tend to have good biocompatibility with the skin and with mucosal membranes.

Of particular interest in transdermal delivery is the delivery of analgesic drugs for the management of moderate to severe pain. Control of the rate and duration of drug delivery is particularly important for transdermal delivery of analgesic drugs to avoid the potential risk of overdose and the discomfort of an insufficient dosage.

One class of analgesics that has found application in a transdermal delivery route is the synthetic opiates, a group of 4-aniline piperidines. The synthetic opiates, eg, fentanyl and certain of its derivatives such as sufentanil, are particularly well-suited for transdermal administration. These synthetic opiates are characterized by their rapid onset of analgesia, high potency, and short duration of action. They are estimated to be 80 and 800 times, respectively, more potent than morphine. These drugs are weak bases, ie, amines, whose major fraction is cationic in acidic media.

In an in vivo study to determine plasma concentration, Thysman and Preat (*Anesth. Analg.* 77 (1993) pp. 61–66) compared simple diffusion of fentanyl and sufentanil to electrotransport delivery in citrate buffer at pH 5. Simple diffusion did not produce any detectable plasma concentration. The plasma levels attainable depended on the maximum flux of the drug that can cross the skin and the drug's pharmacokinetic properties, such as clearance and volume of distribution. Electrotransport delivery was reported to have significantly reduced lag time (ie, time required to achieve peak plasma levels) as compared to passive transdermal patches (1.5 h versus 14 h). The researchers' conclusions were that electrotransport of these analgesic drugs can provide more rapid control of pain than classical patches, and a pulsed release of drug (by controlling electrical current) was comparable to the constant delivery of classical patches. See, also, eg, Thysman et al. *Int. J. Pharma.,* 101 (1994) pp. 105–113; V. Préat et al. *Int J. Pharm.,* 96 (1993) pp. 189–196 (sufentanil); Gourlav et al. *Pain,* 37 (1989) pp. 193–202 (fentanyl); Sebel et al. *Eur. J. Clin. Pharmacol.* 32 (1987) pp. 529–531 (fentanyl and sufentanil). Passive, ie, by diffusion, and electrically-assisted transdermal delivery of narcotic analgesic drugs, such as fentanyl, to induce analgesia, have also both been described in the patent literature. See, for example, Gale et al., U.S. Pat. No. 4,588,580, and Theeuwes et al., U.S. Pat. No. 5,232,438.

In the last several years, management of post-operative pain has looked to delivery systems other than electrotransport delivery. Particular attention has been given to devices and systems which permit, within predetermined limits, the patient to control the amount of analgesic the patient receives. The experience with these types of devices has generally been that patient control of the administration of analgesic has resulted in the administration of less analgesic to the patient than would have been administered were the dosage prescribed by a physician. Self-administered or patient controlled self-administration has become known (and will be referred to herein) as patient-controlled analgesia (PCA).

Known PCA devices are typically electromechanical pumps which require large capacity electrical power sources, eg, alternating current or multiple larger capacity battery packs which are bulky. Due to their bulk and complexity, commercially available PCA devices generally require the patient to be confined to a bed, or some other essentially fixed location. Known PCA devices deliver drug to the patient by means of an intravenous line or a catheter which must be inserted into the intended vein, artery or other organ by a qualified medical technician. This technique requires that the skin barrier be breached in order to administer the analgesic. (See, Zdeb U.S. Pat. No. 5,232,448). Thus, as practiced using commercially available PCA devices, PCA requires the presence of highly skilled medical technicians to initiate and supervise the operation of the PCA device along with its attendant risk of infection. Further, commercially available PCA devices themselves are somewhat painful to use by virtue of their percutaneous (ie, intravenous or subcutaneous) access.

The art has produced little in the way of transdermal electrotransport devices that can compete with the conventional PCAs in terms of the amount of drug delivered to achieve adequate analgesia and in a patient controlled manner. Further, little progress has been made to provide a hydrogel formulation for analgesic electrotransport, particularly fentanyl transdermal electrotransport delivery, that has long term stability and has performance characteristics comparable to the patient controlled electromechanical pumps for, eg, intravenous delivery of analgesic. There is need to provide an analgesic formulation in a suitable device to take advantage of the convenience of electrotransport delivery in a small, self-contained, patient-controlled device.

DESCRIPTION OF THE INVENTION

The present invention provides a method for improved transdermal electrotransport delivery of fentanyl and analogs of fentanyl, particularly sufentanil. As such, the method of the present invention provides a greater degree of efficiency in electrotransport delivery of analgesic fentanyl or sufentanil, concomitantly providing a greater measure of patient safety and comfort in pain management. The foregoing, and other advantages of the present invention, are provided by a method of delivering fentanyl or sufentanil through a body surface (eg, intact skin) by electrotransport from an electrotransport delivery device having a anodic donor reservoir containing an at least partially aqueous solution of a fentanyl/sufentanil salt.

In one aspect, the invention concerns maintaining the concentration of fentanyl or sufentanil salt in the donor reservoir solution at or above a level at which the transdermal fentanyl or sufentanil flux begins to become dependent on the concentration of the drug in solution. For fentanyl, the transdermal electrotransport flux remains independent of fentanyl concentration at or above about 11 to 16 mM substantially throughout the fentanyl electrotransport delivery period. By maintaining the concentration of fentanyl salt solution at or above about 11 to 16 mM in the donor reservoir, the electrotransport flux of the drug remains substantially independent of the drug concentration in the donor reservoir solution and substantially proportional to the level of electrotransport current applied by the delivery device during the electrotransport drug delivery. Maintaining the fentanyl salt solution concentration above about 11 mM, and preferably above about 16 mM ensures a predictable fentanyl flux with a particular applied electrotransport current.

For sufentanil, the transdermal electrotransport flux remains independent of sufentanil concentration at or above about 1.7 mM substantially throughout the sufentanil electrotransport delivery period. By maintaining the concentration of sufentanil salt solution at or above about 1.7 mM in the donor reservoir, the electrotransport flux of the drug remains substantially independent of the drug concentration in the donor reservoir solution and substantially proportional to the level of electrotransport current applied by the delivery device during the electrotransport drug delivery. Maintaining the sufentanil salt solution concentration above about 1.7 mM ensures a predictable sufentanil flux with a particular applied electrotransport current.

In another aspect, the invention provides a donor reservoir formulation for a transdermal electrotransport fentanyl/sufentanil delivery device having an anodic donor electrode comprised of silver, which donor reservoir formulation substantially prevents migration of silver ions into, and discoloration of, the skin of the patient. While the prior art has taught the advantage of using a halide drug salt to prevent the migration of electrochemically generated silver ions (see Untereker et al U.S. Pat. No. 5,135,477), it has now been discovered that for halide salts of fentanyl or sufentanil which are delivered either continuously or intermittently over longer electrotransport delivery periods (eg, periods of at least several hours), the amount of fentanyl/sufentanil halide needed in the donor reservoir in order to prevent this silver migration must be well in excess of the amount of fentanyl/sufentanil which is needed for therapeutic purposes. For fentanyl hydrochloride, the amount of drug needed to prevent silver ion migration has been determined to be at least about 3 times the amount needed for delivery into the patient at least under the specific electrotransport delivery conditions (ie, applied electrotransport current, reservoir size/weight/composition, and time of electrotransport current application) which are described in more detail hereinafter.

In yet another aspect, the present invention concerns a method of administering, fentanyl or sufentanil electrotransport in order to treat moderate-to-severe pain associated with major surgical procedures. We have determined that a transdermal electrotransport dose of about 20 μg to about 60 μg of fentanyl, delivered over a delivery interval of up to about 20 minutes, is therapeutically effective in treating moderate-to-severe post-operative pain in human patients having body weights above about 35 kg. Preferably, the amount of fentanyl delivered is about 35 μg to about 45 μg over a delivery interval of about, 5 to 15 minutes, and most preferably the amount of fentanyl delivered is about 40 μg over a delivery interval of about 10 minutes. Since fentanyl has a relatively short distribution half life once delivered into a human body (ie, about 3 hours), the method of inducing analgesia preferably includes a method for maintaining the analgesia so induced. Thus the method of transdermally delivering fentanyl by electrotransport preferably includes delivering at least 1 additional, more preferably about 10 to 100 additional, and most preferably about 20 to 80 additional, like dose(s) of fentanyl over subsequent like delivery interval(s) over a 24 hour period. The ability to deliver multiple identical doses from a transdermal electrotransport fentanyl delivery device also provides the capability of pain management to a wider patient population, in which different patients require different amounts of fentanyl to control their pain. By providing the capability of administering multiple small transdermal electrotransport fentanyl doses, the patients can titrate themselves to administer only that amount of fentanyl which is needed to contol their pain, and no more.

Other advantages and a fuller appreciation of specific adaptations, compositional variations, and physical attributes of the present invention can be learned from an examination of the following drawings, detailed description, examples, and appended claims.

BRIEF DESCRIPTION OF THE DRAWINGS

The present invention is hereinafter described in conjunction with the appended drawings, in which like designations refer to like elements throughout, and in which.

MODES FOR CARRYING OUT THE INVENTION

Figure 1:
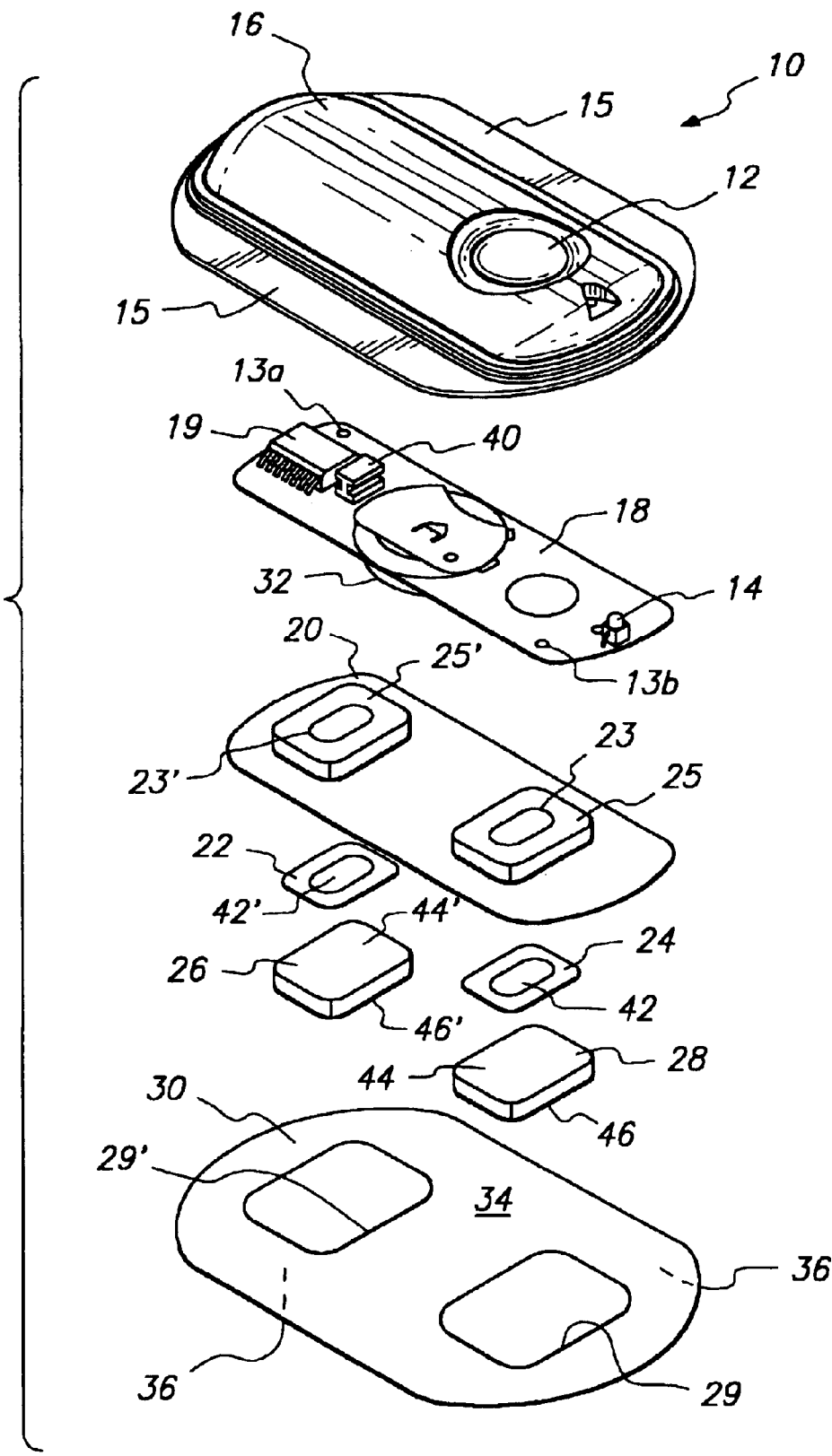
FIG. 1 is a perspective exploded view of an electrotransport drug delivery device in accordance with the present invention.

The present invention relates broadly to improved methods for the transdermal electrotransport delivery of fentanyl or sufentanil, in water soluble salt form, in formulations to achieve a systemic analgesic effect.

Minimum Fentanyl/Sufentanil Concentration to Maintain Predictable Electrotransport Flux In one, aspect, the present invention is characterized by maintaining the transdermal electrotransport fentanyl/sufentanil flux independent of drug concentration in the donor reservoir during the electrotransport drug delivery period. In another aspect, the present invention concerns a fentanyl or sufentanil halide donor reservoir composition, which is adapted to be used in an electrotransport delivery device having a silver anodic donor electrode, which formulation is effective to prevent skin discoloration from silver ions formed during oxidation of the silver anode. In yet another aspect, the present invention provides a fentanyl or sufentanil salt electrotransport delivery device, and a method of using same, to achieve an analgesic effect which is comparable to the effect achieved in known IV accessed patient controlled analgesic pumps.

Concerning the first aspect of the present invention, transdermal electrotransport fentanyl flux begins to become dependent upon the concentration of the fentanyl salt in aqueous solution as the fentanyl salt concentration falls below about 11 to 16 mM. The 11 to 16 mM concentration is calculated based only on the volume of liquid solvent used in the donor reservoir, not on the total volume of the reservoir. In other words, the 11 to 16 mM concentration does not include the volume of the reservoir which is represented by the reservoir matrix (eg, hydrogel or other matrix) material. Furthermore, the 11 to 16 mM concentration is based upon the number of moles of fentanyl salt, not the equivalent number of moles of fentanyl free base, which is contained in the donor reservoir solution.

For fentanyl HCl, the 11 to 16 mM concentration is equivalent to about 4 to 6 mg/mL. Other fentanyl salts (eg, fentanyl citrate) will have slightly differing weight based concentration ranges based on the difference in the molecular weight of the counter ion of the particular fentanyl salt in question.

As the fentanyl salt concentration falls to about 11 to 16 mM, the fentanyl transdermal electrotransport flux begins to significantly decline, even if the applied: electrotransport current remains constant. Thus, to ensure a predictable fentanyl flux with a particular level of applied electrotransport current, the fentanyl salt concentration in the solution contained in the donor reservoir should be maintained above about 11 mM, and preferably above about 16 mM. This aspect of the present invention maintains the fentanyl salt concentration in solution above a minimum level to ensure a predictable transdermal electrotransport flux at any particular applied electrotransport current level.

In addition to fentanyl, water soluble salts of sufentanil also have minimum aqueous solution concentrations below which the transdermal electrotransport flux becomes dependent on concentration of the sufentanil salt in solution. The minimum concentration for sufentanil is about 1.7 mM, which for sufentanil citrate is equivalent to about 1 mg/mL.

As long as there is no binding of the fentanyl/sufentanil to the reservoir matrix material, the particular matrix material chosen as the donor reservoir matrix has little if any effect on the minimum concentration needed to assure predictable transdermal electrotransport fentanyl/sufentanil flux. Hydrogel matrices in particular exhibit no tendency to bind fentanyl or sufentanil and so hydrogels are a preferred class of matrix materials for use with this aspect of the present invention.

Prevention of Siver Migration During Fentanyl/Sufentanil Electrotransport

The second aspect of the invention concerns the delivery of fentanyl or sufentanil from an electrotransport device having a silver donor electrode. Since fentanyl and sufentanil are both bases, the salts of fentanyl and sufentanil are typically acid addition salts, eg, citrate salts, hydrochloride salts, etc. The acid addition salts of fentanyl typically have water solubilities of about 25 to 30 mg/mL. The acid addition salts of sufentanil typically have water solubilities of about 45 to 50 mg/mL. When these salts are placed in solution (eg, aqueous solution), the salts dissolve and form protonated fentanyl or sufentanil cations and counter (eg, citrate or chloride) anions. As such, the fentanyl/sufentanil cations are delivered from the anodic electrode of an electrotransport delivery device. Silver anodic electrodes have been proposed for transdermal electrotransport delivery as a way to maintain pH stability in the anodic reservoir. See for example, Untereker et al U.S. Pat. No. 5,135,477 and Petelenz et al U.S. Pat. No. 4,752,285. These patents also recognize one of the shortcomings of using a silver anodic electrode in an electrotransport delivery device, namely that the application of current through the silver anode causes the silver to become oxidized ($Ag \rightarrow Ag^+ + e^-$) thereby forming silver cations which compete with the cationic drug for delivery into the skin by electrotransport. Silver ion migration into the skin results in a transient epidermal discoloration (TED) of the skin. In addition to these patents, Phipps et al PCT/US95/04497 filed on Apr. 7, 1995 teaches the use of supplementary chloride ion sources in the form of high molecular weight chloride resins in the donor reservoir of a transdermal electrotransport delivery device. While these resins are highly effective at providing sufficient chloride for preventing silver ion migration, and the attendant skin discoloration, these resins can also have adverse reactions with either the drug being delivered (ie, binding of drug to the resin) and/or with the skin of the patient (ie, contributing to skin irritation reactions). Thus, for the purposes of the following discussion, the donor reservoir formulations of the present invention will be assumed to be substantially free of such secondary chloride ion source resins. While the Untereker and Petelenz patents teach that providing a cationic drug in the form of a halide salt prevents the migration of silver ions (ie, by reacting the silver ions with the halide counter ion of the drug to form a water insoluble silver halide precipitate; $Ag^+ + X^- \rightarrow AgX$), we have surprisingly discovered that a significant excess (ie, an amount well in excess of the fentanyl halide salt needed to be delivered to the patient for purposes of achieving analgesia) of fentanyl halide must be provided in a donor reservoir of an electrotransport fentanyl delivery device in order to prevent silver ion migration. This is especially true for those transdermal electrotransport delivery devices which are adapted to apply electrotransport current for extended periods of time, eg, longer than about 6 hours.

In general, the "excess" amount of fentanyl halide needed to prevent silver ion migration will be highly dependent upon a number of factors including the particular halide salt used (eg, chloride, fluoride, bromide or iodide salt of the drug), the level of applied electrotransport current, the size/weight/composition of the donor reservoir, the applied current density level and the length of time over which the electrotranport current is applied. We have determined delivering fentanyl hydrochloride from polyvinyl alcohol based donor reservoirs which are used to deliver fentanyl for periods of up to about 15 hours, that the amount of fentanyl HCl needed to prevent silver ion migration during electrotransport delivery is about 2 to 3 times the amount of fentanyl HCl needed for delivery into the patient over that same period of time for purposes of inducing and maintaining analgesia.

In the specific case of an electrotransport delivery device having a polyvinyl alcohol based donor reservoir containing fentanyl hydrochloride and having a total weight (on a hydrated basis) of about 0.3 to 0.8 g, which device (1) has an anodic donor electrode comprised of silver (eg, silver foil or silver powder-loaded polymer film) which is in electrical contact with the donor reservoir, (2) has an electrical power source which applies a DC current of about 190 $\mu$A to 230

μA to the donor and counter electrodes, (3) applies a current density, measured as the total applied current divided by the skin contact area of the donor reservoir, of less than about 0.3 mA/cm², and (4) is capable of applying such current for up to about eighty separate delivery intervals of about 8 to about 12 minutes duration, the fentanyl HCl loading needed to induce and maintain analgesia is about 2.5 to 3.5 mg, yet the fentanyl HCl loading needed to prevent TED is at least about 8 to 10 mg, and preferably at least about 11 to 13 mg. More specifically in the case of an electrotransport delivery device having a polyvinyl alcohol based donor reservoir containing fentanyl hydrochloride and having a total weight (on a hydrated basis) of about 0.5 to 0.8 g, which device applies a DC current of about 210 μA to the electrodes, and is capable of applying such current for up to about eighty separate delivery intervals of about 10 minutes duration, the fentanyl HCl loading needed to induce and maintain analgesia is about 3 mg, yet the fentanyl HCl loading needed to prevent TED is at least about 9 mg, and preferably at least about 12 mg.

In order to determine the loading of a halide salt of fentanyl other than fentanyl HCl, it is only necessary to supply an equivalent molar amount of halide ions to the reservoir since the silver halide salts have fairly uniformly low water solubility. For example, the loading of 8 to 10 mg of fentanyl HCl corresponds to a molar loading of about 20 to 25 μmoles. Thus, about 20 to 25 μmoles of any of the other fentanyl halides (ie, fentanyl fluoride, fentanyl bromide or fentanyl iodide) will provide an equivalent degree of silver migration prevention as fentanyl HCl.

In addition to fentanyl, "excess" amounts of sufentanil halide salts also can be used to prevent silver ion migration. Because sufentanil is about 7 to 10 times more potent than fentanyl, only about 0.1 to 0.14 times the fentanyl dose is needed to achieve an equivalent level of analgesia. However, because the transdermal electrotransport delivery efficiency of sufentanil (ie, the rate of sufentanil delivered per unit of applied electrotransport current) is only about one-third that of fentanyl, the applied electrotransport current needed to achieve the same level of analgesia with sufentanil is about 0.3 to 0.4 times that needed for fentanyl. Thus, the "excess" amount of sufentanil chloride needed to prevent silver ion migration during electrotransport delivery of sufentanil is correspondingly reduced to about 6 to 10 μmoles or about 2.4 to 4 mg. The amount of sufentanil HCl loading needed to prevent silver ion migration, relative to the loading needed to achieve an analgesic effect in a patient, is at least about 4 times the analgesically effective loading.

As long as the reservoir matrix material has substantially no silver ion binding capacity (ie, by means of a fixed anionic (eg, COO) moiety as is found in cation exchange membranes), the particular matrix material chosen as the donor reservoir matrix has little if any effect on the minimum loading of halide salts of fentanyl and sufentanil which is effective to prevent silver ion migration into the patient's skin. Hydrogel matrices in particular exhibit little or no tendency to bind silver ions and so are a preferred matrix material for use with this aspect of the present invention.

Transdermal Electrotransport Fentanyl/Sufentanil Dosing for Inducing and Maintaining Analgesia In another aspect, the present invention provides a method and electrotransport delivery device for delivering fentanyl or sufentanil through a body surface, eg, skin, to achieve an analgesic effect. The fentanyl or sufentanil salt is provided in a donor reservoir of an electrotransport delivery device as an aqueous salt solution.

The dose of fentanyl delivered by transdermal electrotransport is about 20 μg to about 60 μg over a delivery time of up to about 20 minutes in human patients having body weights of 35 kg or greater. Preferred is a dosage of about 35 μg to about 45 μg, and most preferred is a dosage of about 40 μg for the delivery period. The method of the invention further preferably includes delivery of about 10 to 100, and more preferably about 20 to 80 additional like doses over a period of 24 hours in order to achieve and maintain the analgesic effect.

The dose of sufentanil delivered by transdermal electrotransport is about 2.3 μg to about 7.0 μg over a delivery time of up to about 20 minutes in human patients having a body weights of 35 kg or greater. Preferred is a dosage of about 4 μg to about 5.5 μg, and most preferred is a dosage of about 4.7 μg for the delivery period. The method of the invention further preferably includes delivery of about 10 to 100, and more preferably about 20 to 80 additional like doses over a period of 24 hours in order to achieve and maintain the analgesic effect.

The fentanyl/sufentanil salt-containing anodic reservoir formulation for transdermally delivering the above mentioned doses of fentanyl/sufentanil by electrotransport is preferably comprised of an aqueous solution of a water soluble fentanyl/sufentanil salt such as HCl or citrate salts. Most preferably, the aqueous solution is contained within a hydrophilic polymer matrix such as a hydrogel matrix. The fentanyl/sufentanil salt is present in an amount sufficient to deliver the above mentioned doses transdermally by electrotransport over a delivery period of up to about 20 minutes, to achieve a systemic analgesic effect. The fentanyl/sufentanil salt typically comprises about 1 to 10 wt % of the donor resevoir formulation (including the weight of the polymeric matix) on a fully hydrated basis, and more preferably about 1 to 5 wt % of the donor reservoir formulation on a fully hydrated basis. Although not critical to this aspect of the present invention, the applied electrotransport current density is typically in the range of about 50 to 150 μA/cm² and the applied electrotransport current is typically in the range of about 150 to 240 μA.

The anodic fentanyl/sufentanil salt-containing hydrogel can suitably be made of any number of materials but preferably is comprised of a hydrophilic polymeric material, preferably one that is polar in nature so as to enhance the drug stability. Suitable polar polymers for the hydrogel matrix comprise a variety of synthetic and naturally occurring polymeric materials. A preferred hydrogel formulation contains a suitable hydrophilic polymer, a buffer a humectant, a thickener, water and a water soluble fentanyl or sufentanil salt (eg, HCl salt). A preferred hydrophilic polymer matrix is polyvinyl alcohol such as a washed and fully hydrolyzed polyvinyl alcohol (PVOH), eg, Mowiol 66-100 commercially available from Hoechst Aktiengesellschraft. A suitable buffer is an ion exchange resin which is a copolymer of methacrylic acid and divinylbenzene in both an acid and salt form. One example of such a buffer is a mixture of Polacrilin (the copolymer of methacrylic acid and divinyl benzene available from Rohm & Haas, Philadelphia, Pa.) and the potassium salt thereof. A mixture of the acid and potassium salt forms of Polacrilin functions as a polymeric buffer to adjust the pH of the hydrogel to about pH 6. Use of a humectant in the hydrogel formulation is beneficial to inhibit the loss of moisture from the hydrogel. An example of a suitable humectant is guar gum. Thickeners are also beneficial in a hydrogel formulation. For example, a polyvinyl alcohol thickener such as hydroxypropyl methylcellulose (eg, Methocel K100MP available from Dow Chemical, Midland, Mich.) aids in modifying the rheology of a hot polymer solution as it is dispensed into a mold or cavity. The hydroxypropyl methylcellulose increases in viscosity on cooling and significantly reduces the propensity of a cooled polymer solution to overfill the mold or cavity.

In one preferred embodiment, the anodic fentanyl/sufentanil salt-containing hydrogel formulation comprises about 10 to 15 wt % polyvinyl alcohol, 0.1 to 0.4 wt % resin buffer, and about 1 to 2 wt % fentanyl or sufentanil salt, preferably the hydrochloride salt. The remainder is water and ingredients such as humectants, thickeners, etc. The polyvinyl alcohol (PVOH)-based hydrogel formulation is prepared by mixing all materials, including the fentanyl or sufentanil salt, in a single vessel at elevated temperatures of about 90° C. to 95° C. for at least about 0.5 hr. The hot mix is then poured into foam molds and stored at freezing temperature of about −35° C. overnight to cross-link the PVOH. Upon warming to ambient temperature, a tough elastomeric gel is obtained suitable for fentanyl electrotransport.

The hydrogel formulations are used in an electrotransport device such as described hereinafter. A suitable electrotransport device includes an anodic donor electrode, preferably comprised of silver, and a cathodic counter electrode, preferably comprised of silver chloride. The donor electrode is in electrical contact with the donor reservoir containing the aqueous solution of a fentanyl/sufentanil salt. As described above, the donor reservoir is preferably a hydrogel formulation. The counter reservoir also preferably comprises a hydrogel formulation containing a (eg, aqueous) solution of a biocompatible electrolyte, such as citrate buffered saline. The anodic and cathodic hydrogel reservoirs preferably each have a skin contact area of about 1 to 5 cm² and more preferably about 2 to 3 cm². The anodic and cathodic hydrogel reservoirs preferably have a thickness of about 0.05 to 0.25 cm, and more preferably about 0.15 cm. The applied electrotransport current is about 150 μA to about 240 μA, depending on the analgesic effect desired. Most preferably, the applied electrotransport current is substantially constant DC current during the dosing interval.

Reference is now made to FIG. 1 which depicts an exemplary electrotransport-device which can be used in accordance with the present invention. FIG. 1 shows a perspective exploded view of an electrotransport device 10 having an activation switch in the form of a push button switch 12 and a display in the form of a light emitting diode (LED) 14. Device 10 comprises an upper housing 16, a circuit board assembly 1, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin Upper housing 16 is preferably composed of an injection moldable elastomer (eg, ethylene vinyl acetate). Printed circuit board assembly 18 comprises an integrated circuit 19 coupled to discrete electrical components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a battery 32, which is preferably a button cell battery and most preferably a lithium cell. Other types of batteries may also be employed to power device 10.

The circuit outputs (not shown in FIG. 1) of the circuit board assembly 18 make electrical contact with the electrodes 24 and 22 through openings 23,23' in the depressions 25,25' formed in lower housing, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30. Upon depression of push button switch 12, the electronic circuitry on circuit board assembly 18 delivers a predetermined DC current to the electrodes/reservoirs 22,26 and 24,28 for a delivery interval of predetermined length, eg, about 10 minutes. Preferably, the device transmits to the user a visual and/or audible confirmation of the onset of the drug delivery, or bolus, interval by means of LED 14 becoming lit and/or an audible sound signal from, eg, a "beeper". Analgesic drug, eg fentanyl, is then delivered through the patient's skin, eg, on the arm, for the predetermined (eg, 10 minute) delivery interval. In practice, a user receives feedback as to the onset of the drug delivery interval by visual (LED 14 becomes lit) and/or audible signals (a beep from the "beeper").

Anodic electrode 22 is preferably comprised of silver and cathodic electrode 24 is preferably comprised of silver chloride. Both reservoirs 26 and 28 are preferably comprised of polymer hydrogel materials as described herein. Electrodes 22, 24 and reservoirs 26, 28 are retained by lower housing 20. For fentanyl and sufentanil salts, the anodic reservoir 26 is the "donor" reservoir which contains the drug and the cathodic reservoir 28 contains a biocompatible electrolyte.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (eg, polyethylene) which can be easily molded to form depressions 25,25' and cut to form openings 23,23'. The assembled device 10 is preferably water resistant (ie, splash proof) and is most preferably waterproof. The system has a low profile that easily conforms to the body thereby allowing freedom of movement at, and around, the wearing site. The anode/drug reservoir 26 and the cathode/salt reservoir 28 are located on the skin-contacting side of device 10 and are sufficiently separated to prevent accidental electrical shorting during normal handling and use.

The device 10 adheres to the patient's body surface (eg, skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (eg, 24-hour) wear period. Upper adhesive side 34 adheres to lower housing 20 and retains the electrodes and drug reservoirs within housing depressions 25,25' as well as retains lower housing 20 attached to upper housing 16.

The push button switch 12 is located on the top side of device 10 and is easily actuated through clothing. A double press of the push button switch 12 within a short period of time, eg, three seconds, is preferably used to activate the device 10 for delivery of drug, thereby minimizing the likelihood of inadvertent actuation of the device 10.

Upon switch activation an audible alarm signals the start of drug delivery, at which time the circuit supplies a predetermined level of DC current to the electrodes/reservoirs for a predetermined (eg, 10 minute) delivery interval. The LED 14 remains "on" throughout the delivery interval indicating that the device 10 is in an active drug delivery mode. The battery preferably has sufficient capacity to continuously power the device 10 at the predetermined level of DC current for the entire (eg, 24 hour) wearing period.

The present invention is further explained by the following examples which are illustrative of, but do not limit the scope of, the present invention.

EXAMPLE 1

The following experiment was conducted in order to determine the necessary minimum concentration of fentanyl salt in a donor reservoir of a transdermal electrotransport delivery device in order to ensure that the transdermal electrotransport fentanyl flux remains approximately proportional to the level of applied electrotransport current.

Anodic donor reservoir gels, having varying loadings of fentanyl HCl, were prepared having the following composition:

| Material | (wt %) |
|---|---|
| Water | 81.3 |
| PVOH | 15.0 |
| Fentanyl HCl | 1.7 |
| Polacrilin | 0.1 |
| 0.5 N NaOH | 1.9 |

The combination of Polacrilin and NaOH acted as a buffer to maintain the pH of the gels around 5.5. Polacrilin (also known as Amberlite IRP-64) is sold by Rohm & Haas of Philadelphia, Pa. The materials were mixed in a beaker at elevated temperature of 90° C. to 95° C., poured into foam molds and stored overnight at −35° C. to cross-link the PVOH. The gels had a skin contact area of 2 cm$^2$ and a thickness of 1.6 mm. The gels had a fentanyl HCl concentration of 21 mg/mL of water. A silver foil anodic electrode was laminated to one surface of the gels.

The transdermal electrotransport fentanyl flux from these gels was measured by in vitro flux studies using a two-compartment diffusion cell and human cadaver skin. The gels were mounted on the stratum corneum side of heat stripped human cadaver epidermis taken from back skin samples. The other side of the epidermis was exposed to a receptor compartment, having a volume of 4 cm$^2$, and filled with one tenth strength Dulbecco's phosphate buffered saline (pH 7.4). A counter electrode comprised of a polyisobutylene film loaded with silver chloride powder was placed in the receptor compartment.

The donor and counter electrodes were electrically connected to a galvanostat which was set to apply a constant DC current of 200 μA (ie, 100 μA/cm$^2$). The current was applied continuously for 16 hours and the receptor compartment was sampled every hour over the 16 hour period.

Six identical flux experiments were run with different skin samples and the transdermal flux was averaged over the 6 runs. The transdermal fentanyl flux increased over the first 8 hours of current application, after which the flux remained approximately constant (ie, steady state flux was reached after 8 hours). The fentanyl concentration was estimated by subtracting the amount of fentanyl delivered through the skin into the receptor solution from the original fentanyl content in the donor gel, and dividing by the weight of water in the gel.

Figure 2:
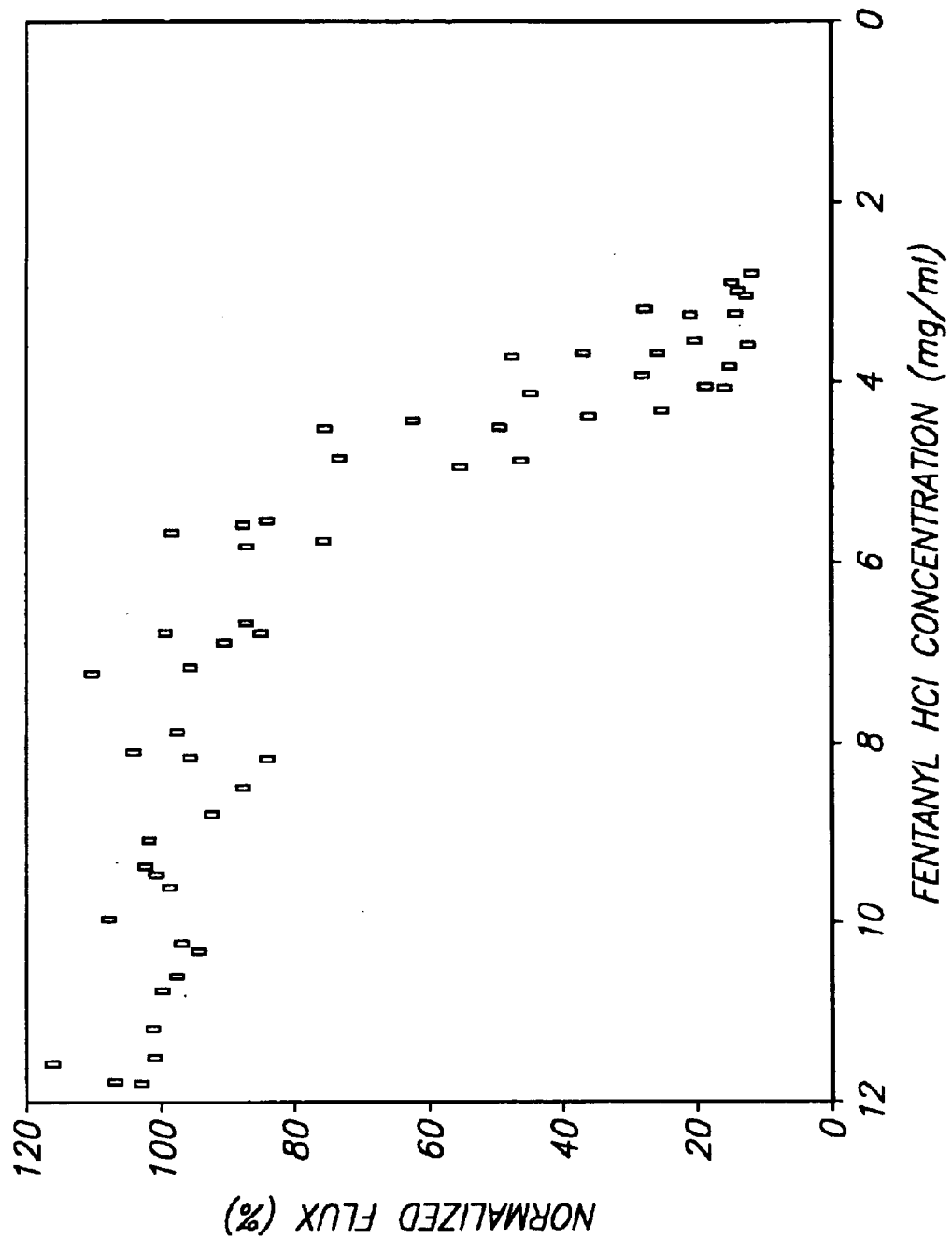
FIG. 2 is a graph of normalized transdermal electrotransport flux versus concentration of fentanyl HCl in aqueous solution.

The normalized transdermal fentanyl flux, calculated as a percentage of the steady state transdermal flux, was plotted versus fentanyl concentration in the gel, and is shown in FIG. 2. As can be seen from FIG. 2, the normalized flux remains at or near 100% at fentanyl HCl concentrations above about 6 mg/mL. The normalized flux begins to drop off as the fentanyl HCl concentration falls below 6 mg/mL and particularly below about 4 mg/mL. These results show that as the fentanyl HCl concentration falls below about 6 mg/mL, a more significant portion of the applied electrotransport current is carried by ions other than fentanyl ions and the fentanyl flux is more dependent on the fentanyl HCl concentration. Thus, to ensure a predictable fentanyl flux with a particular level of applied electrotransport current, the fentanyl HCl concentration in the donor reservoir is preferably maintained above about 6 mg/mL.

EXAMPLE 2

The following study was conducted to determine the amount of fentanyl hydrochloride drug loading which is necessary to prevent silver migration, resulting in transient epidermal discoloration, from a transdermal fentanyl electrotransport delivery device having a donor reservoir gel weighing about 0.6 g and having a skin contact area of about 2.8 cm$^2$, which device is worn for a period of up to 24 hours and which applies an electrotransport current of 240 μA (ie, a current density of 87 μA/cm$^2$) over a is delivery interval of about 10 minutes to deliver a 40 μg dose, and which can deliver up to 80 of such doses over the 24 hour wearing period. Thus, the device has the ability to deliver up to 3.2 mg of fentanyl (80×40 μg=3.2 mg) for therapeutic purposes.

Fentanyl HCl-containing polyvinyl alcohol (PVOH) hydrogel-based donor reservoirs, each reservoir having a total weight of about 0.15 g, were made with the following composition:

| Material | (wt %) |
|---|---|
| Water | 80.8 |
| PVOH | 15.0 |
| Fentanyl HCl | 2.0 |
| Polacrilin | 0.1 |
| 0.5 N NaOH | 2.1 |

The materials were mixed in a jacketed beaker at 90° C. and then 0.15 g aliquots of the liquid gel were dispensed into foam molds and frozen overnight at temperatures ranging from −15 to −50° C. The gels had a disk shape with an area of 1.0 cm$^2$ and a thickness of 1.6 mm.

A silver foil was laminated to one surface of each of the gels to form an anodic donor electrode assembly comprised of the silver foil anode and the fentanyl containing gel reservoir. Counter electrode assemblies were made using similarly sized PVOH gels which contained citrate buffered saline (pH 4). A silver chloride cathodic electrode (ie, silver chloride powder-loaded polyisobutylene film) was laminated to one surface of the counter gels. The electrodes were electrically connected to custom made power sources which applied a constant DC current of 240 μA (87 μA/cm$^2$).

The electrotransport systems were applied to the upper outer arms of six male volunteers and worn for a period of 15 hours, which is about 10% longer than the maximum time of current application from this system (ie, 80×10 minutes= 13.3 hrs). Over the 15 hour wearing period, the systems applied current continuously, after which the systems were removed and the arm of each subject was closely examined to determine if transient epidermal discoloration (TED), caused by migration of silver ions formed in the anodic electrode assembly, had occurred. The subjects were again examined one hour and again at 24 hours after system removal to confirm the initial TED reading. In all six subjects, no TED occurred at the site of attachment of the anodic electrode assembly. This indicates that a fentanyl HCl loading of about 1.8 to 2 wt %, or about 3 mg in these gels, provides a sufficient quantity of chloride ions to prevent migration of silver ions, formed by oxidation of the silver anode, into the skin of the patient over the 15 hour wearing period. Thus, an electrotransport system which applies the same level of electrotransport current over a maximum dosing period of 13.3 hours will likewise exhibit no TED, even under conditions of maximum usage. The 2 wt % fentanyl HCl loading in these PVOH-based donor gel reservoirs can be scaled-up to larger reservoirs. Thus, for a fentanyl HCl-containing PVOH-based donor reservoir having a total weight of about 0.6 g, the reservoir containing substantially no other source of chloride ions other than the drug counter ions, the fentanyl HCl loading should be at least about 11 mg (ie, 1.8 wt %×0.6 g=11 mg) even though the maximum amount of fentanyl which can be delivered from the device over the 24 hour wearing period is only about 3.2 mg fentanyl. Thus, in order to prevent silver migration in this device under conditions of maximum usage, an excess amount of fentanyl HCl must be loaded into the anodic donor reservoir, which excess loading is about 3 to 4 times the amount of fentanyl needed for therapeutic purposes.

EXAMPLE 3

The following studies were conducted to determine the transdermal electrotransport dosing level required to achieve an acceptable level of analgesia in human patients suffering from moderate to severe post-operative pain. The study was conducted in 132 post-operative male and female patients who were expected to have moderate to severe pain after surgery, including orthopedic (shoulder, knee, long bone) and abdominal (urological, gynecological) surgeries. The patients wore one of two different electrotransport fentanyl HCl delivery devices on the upper arm for 24 hours following surgery. Both devices applied electrotransport current for a delivery interval of 10 minutes upon activating a push button switch on the device. The first device, worn by 79 of the 132 patients, applied an electrotransport current of 150 $\mu$A which delivered an average fentanyl dose of 25 $\mu$g over the 10 minute delivery interval. The second device, worn by 53 of the 132 patients, applied an electrotransport current of 240 $\mu$A which delivered an average fentanyl dose of 40 $\mu$g over the 10 minute delivery interval.

In both devices, the patients could self-administer up to 6 doses every hour. Patients using the first (ie, 25 $\mu$g dose) device could apply a maximum of 144 doses. Patients using the second (ie, 40 $\mu$g dose) device were allowed to apply up to a maximum number of 80 doses.

Both devices were two-part systems which included a reusable electronic controller and a single use/disposable drug-containing unit. Each drug unit contained an anodic fentanyl HCl-containing donor gel and a cathodic saline-containing counter gel. All gels had a skin contact area of 2 cm$^2$ and a thickness of 0.16 cm. The approximate weight of the donor gels was 350 mg. The anodic donor gels in the 25 $\mu$g dose and 40 $\mu$g dose systems were the same size and composition, only the applied electrotransport current level was different. The cathodic counter electrode assemblies each had a PVOH based gel which contained citrate buffered saline. A silver chloride cathodic electrode was laminated to one surface of the counter gel. The 25 $\mu$g and 40 $\mu$g dose anodic gels had the following composition:

| Material | (wt %) |
| --- | --- |
| Water | 73.2 |
| PVOH | 10.0 |
| Fentanyl HCl | 1.4 |
| Polacrilin | 0.3 |
| Polacrilin potassium | 0.1 |
| Glycerin | 5.0 |
| Cholestyramine resin | 10.0 |

All patients were initially titrated to an acceptable level of analgesia with intravenous (IV) fentanyl in the recovery room immediately following surgery. Within 3 hours after surgery when the patients had met the usual institutional standards for discharge from the recovery room and were able to operate their worn electrotransport delivery device, the patients were moved to a ward where they could self administer fentanyl by transdermal electrotransport for the management of their pain. In the event the electrotransport fentanyl delivery regimen was insufficient to control pain, the patients were retitrated with supplemental fentanyl through IV administration to achieve adequate analgesia.

In the 25 $\mu$g dose group, 38 of 79 patients (ie, 48%) required no supplemental IV fentanyl after leaving the recovery room. In the 40 $\mu$g dose group, 47 of 53 patients (ie, 89%) required no supplemental IV fentanyl after leaving the recovery room. Based on these percentages, it was determined that the 25 $\mu$g dose regimen was insufficient, and the 40 $\mu$g dose regimen was sufficient, to treat the pain associated with these types of surgical procedures in a majority of the patients tested. Based on the fact that the 25 $\mu$g dose regimen was analgesically effective for about half the patients, it is likely that this lower dose would be effective in treating less severe acute pain such as that experienced with hernia repair, kidney stones, arthritis pain, laparascopic procedures, and other conditions involving less severe pain than that associated with major surgeries.

Pain intensity was assessed at baseline immediately before activation of the first on-demand dose and again at times 0.5, 1, 2, 3, 4, 6, 8, 12, 16, 20 and 24 hours after the devices were first activated. The patients were asked to assess pain intensity by marking on a 10 cm long strip, containing a scale of 1 to 100, with 1 being associated with no pain and 100 being associated with the most severe intensity pain. The quality of analgesia was evaluated by a categorical rating of excellent, good, fair or unsatisfactory according to the same time schedule as that for the pain intensity measurements.

Figure 3:
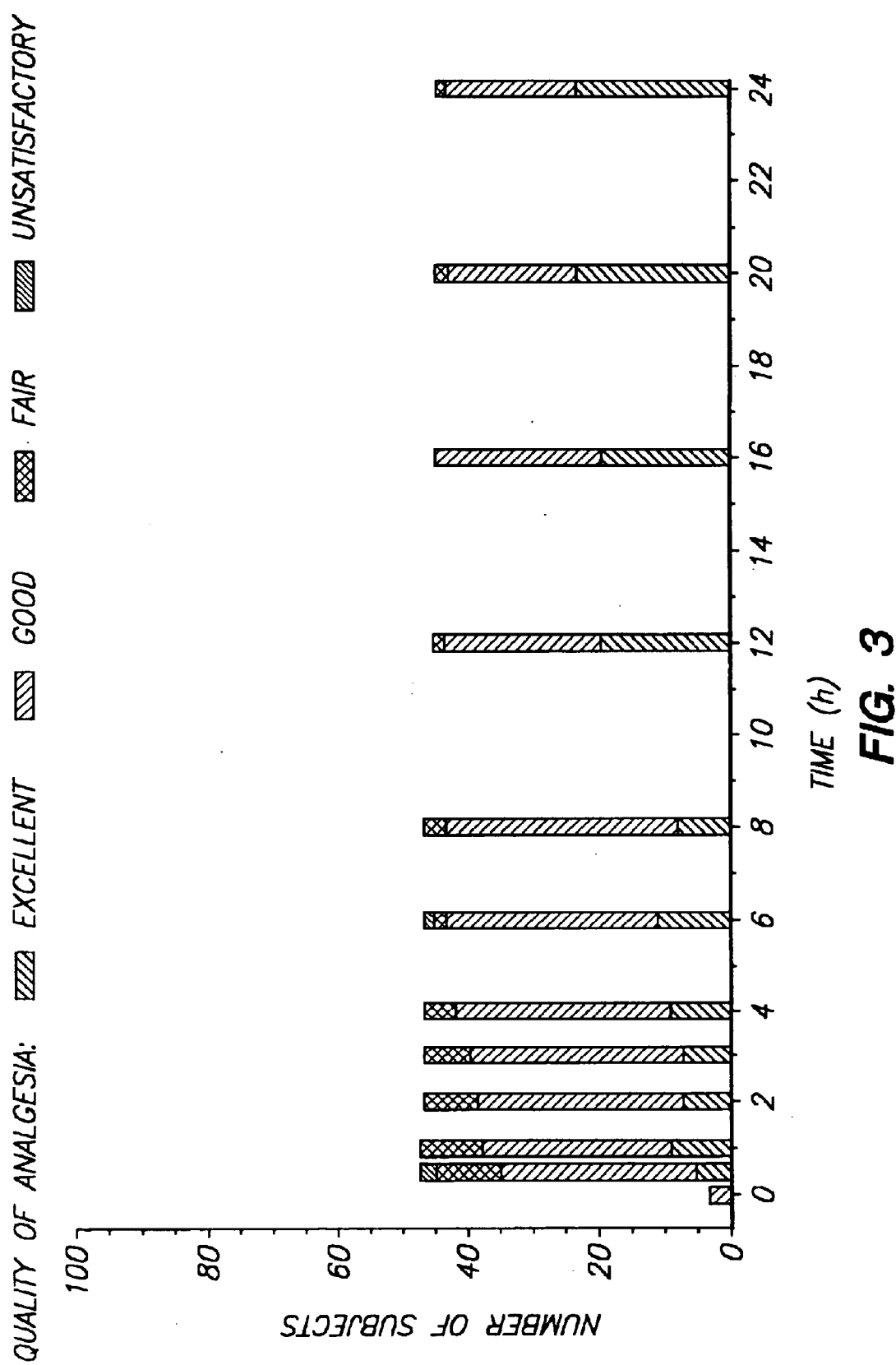
FIG. 3 is a graph illustrating quality of analgesia in patients administered with transdermal electrotransport fentanyl as a function of time.
Figure 4:
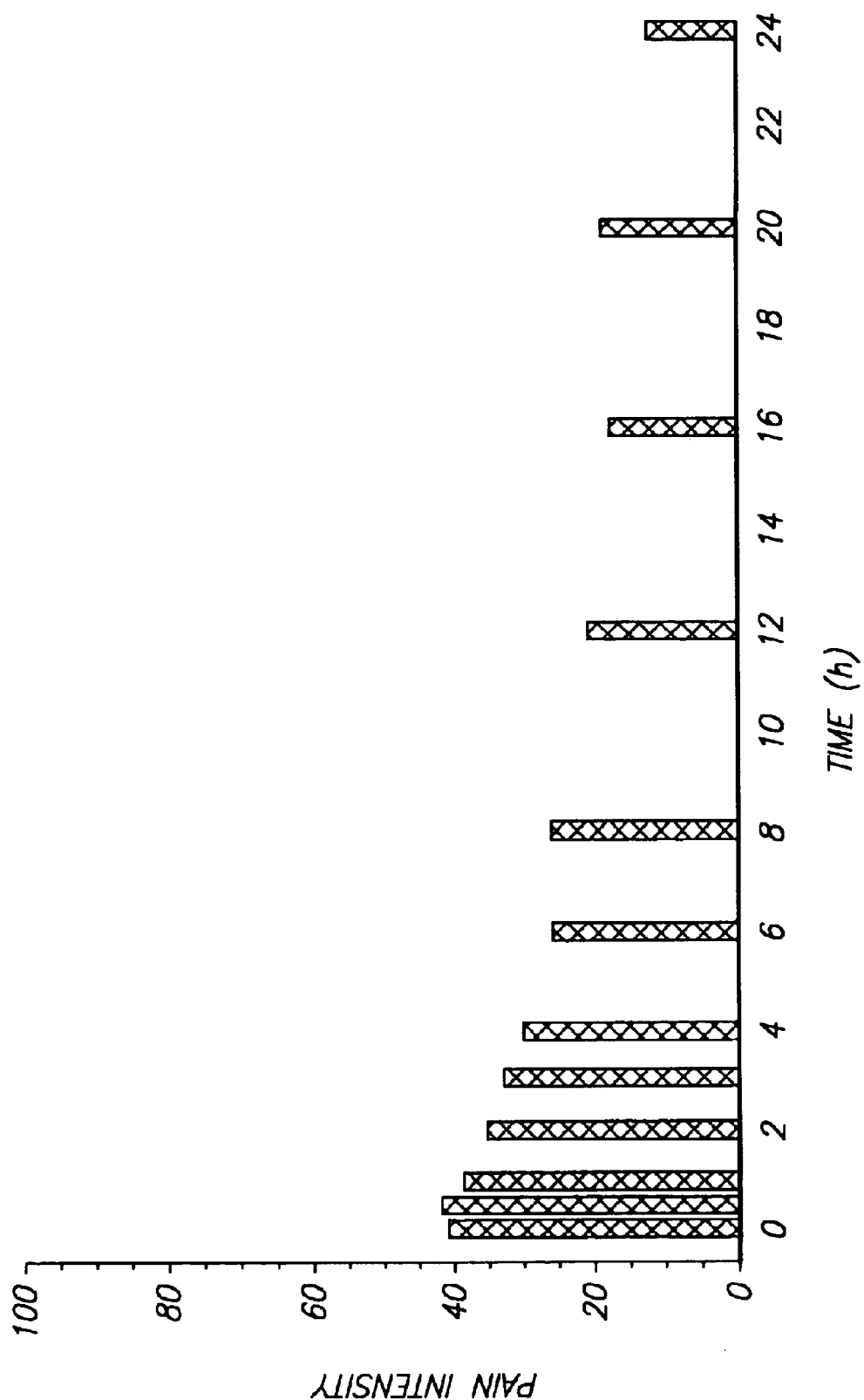
FIG. 4 is a graph illustrating pain intensity experienced by patients administered transdermal electrotransport fentanyl as a function of time.

The quality of analgesia and pain intensity data for the 53 patients using the 40 $\mu$g dose electrotransport devices are shown in FIGS. 3 and 4, respectively.

Skin sites beneath the anode and cathode gels were assessed at 1, 6 and 24 hours following removal of the devices and evaluated for topical (eg, irritation) effects. The topical effects data are shown in Table 1.

TABLE 1

| Hours Post Removal | ETS Skin Site | Score | Edema (%) | Erythema (%) | Extent of Erythema (%) | Itching (%) | Papules (%) | Pustules (%) |
|---|---|---|---|---|---|---|---|---|
| 1 | Anode | 0 | 74 | 15 | 19 | 91 | 92 | 100 |
|   |   | 1 | 8 | 49 | 32 | 6 | 6 | 0 |
|   |   | 2 | 19 | 36 | 49 | 4 | 2 | 0 |
|   | Cathode | 0 | 92 | 72 | 74 | 94 | 94 | 100 |
|   |   | 1 | 8 | 19 | 13 | 4 | 6 | 0 |
|   |   | 2 | 2 | 9 | 13 | 2 | 0 | 0 |
| 6 | Anode | 0 | 74 | 15 | 17 | 89 | 92 | 100 |
|   |   | 1 | 11 | 43 | 34 | 8 | 8 | 0 |
|   |   | 2 | 15 | 40 | 49 | 4 | 0 | 0 |
|   |   | 3 | 0 | 2 | 0 | 0 | 0 | 0 |
|   | Cathode | 0 | 92 | 68 | 68 | 91 | 91 | 100 |
|   |   | 1 | 4 | 19 | 13 | 9 | 8 | 0 |
|   |   | 2 | 4 | 9 | 19 | 0 | 4 | 0 |
|   |   | 3 | 0 | 4 | 0 | 0 | 0 | 0 |
| 24 | Anode | 0 | 83 | 34 | 36 | 91 | 96 | 98 |
|   |   | 1 | 9 | 40 | 38 | 8 | 4 | 2 |
|   |   | 2 | 8 | 26 | 38 | 2 | 0 | 0 |
|   |   | 3 | 0 | 0 | 0 | 0 | 0 | 0 |
|   | Cathode | 0 | 91 | 70 | 70 | 91 | 89 | 98 |
|   |   | 1 | 6 | 19 | 15 | 8 | 8 | 0 |
|   |   | 2 | 4 | 8 | 15 | 2 | 4 | 2 |
|   |   | 3 | 0 | 4 | 0 | 0 | 0 | 0 |

Erythema:
0 = None
1 = Barely perceptible redness
2 = Definite redness
3 = "Beef" redness
Itching:
0 = None
1 = Mild
2 = Moderate
3 = Severe
Edema, Papules, Pustules, Extent of Erythema:
0 = None
1 = <50% of occluded area
2 = >50% of occluded area

EXAMPLE 4

Two fentanyl hydrochrloide-containing anodic donor reservoir PVOH-based gels were made having the following compositions:

Donor Gel Formulations:

| Material | wt % | wt % |
|---|---|---|
| Purified Water | 86.3 | 85.3 |
| Washed PVOH | 12.0 | 12.0 |
| Fentanyl HCL | 1.7 | 1.7 |
| Hydroxy Methylcellulose | — | 1.0 |

With both formulations, the water and PVOH are mixed at a temperature between 92° C. and 98° C. followed by the addition of fentanyl hydrochloride and subsequent further mixing. The liquid gel was then pumped into foam molds having a disc-shaped cavity. The molds were placed in a freezer overnight at −35° C. to cross-link the PVOH. The gels can be used as anodic donor reservoirs suitable for transdermal electrotransport fentanyl delivery.

In summary, the present invention provides a method for improving the transdermal electrotransport of water soluble salts of fentanyl, and sufentanil which are preferably delivered from an electrotransport device having a silver anodic donor electrode and a hydrogel based donor reservoir. The electrotransport device is preferably a patient-controlled device. The hydrogel formulation contains a drug concentration which is sufficient to maintain transdermal electrotransport drug flux for a predetermined current level, to inhibit silver ion migration to the skin of a wearer of the electrotransport device and thus, prevent transient epidermal discoloration, and to provide an acceptable level of analgesia.

What is claimed is:

1. A method for delivering an active agent through a body surface by electrotransport comprising the steps of:
   a) providing an electrotransport delivery device having a silver anodic donor electrode, a cathodic counter electrode, and a donor reservoir containing a loading amount of the analgesic drug in electrical contact with the donor electrode, wherein the donor reservoir is substantially free of sources of halide other than the selected analgesic drug halide salt, the device adapted to deliver a predetermined maximum total amount of analgesic drug over a period of time, the loading amount being at loan about two times the predetermined maximum total amount to prevent transient epidermal discoloration; and
   b) delivering only up to the maximum total amount of the analgesic drug; wherein the analgesic drug is selected from the group consisting of fentanyl halide salts and sufentanil halide salts thereby avoiding transient epidermal discoloration.

2. The method of claim 1, wherein the donor reservoir comprises a hydrogel containing an aqueous fentanyl salt solution, and further comprising the step of maintaining the solution fentanyl concentration above 6 mg/mL in the hydrogel.

3. The method of claim 1, wherein the body surface is intact skin and the period of time is at least 6 hours.

4. The method of claim 1, wherein the body surface is intact human skin.

5. The method of claim 1, wherein the delivery of the analgesic drug through the body surface is substantially proportional to a level of current applied by the delivery device during the iontophoretic drug delivery.

6. The method of claim 5, wherein the level of current applied by the delivery device ranges between about 150 $\mu$A to about 240 $\mu$A.

7. The method of claim 5, wherein the level of current applied by the delivery device ranges between about 150 $\mu$A to about 190 $\mu$A.

8. The method of claim 5, wherein the level of current applied by the delivery device ranges between about 190 $\mu$A to about 240 $\mu$A.

9. The method of claim 1; wherein the step of delivering only up to a maximum total amount of the analgesic drug comprises delivering multiple predetermined dose amounts.

10. The method of claim 9, wherein the step of delivering a predetermined dose amount comprises applying a level of current for a delivery interval of up to about 20 minutes.

11. The method of claim 10, wherein the step of delivering a predetermined dose amount comprises applying a level of current for a delivery interval of about 8 to about 12 minutes.

12. The method of claim 9, wherein delivering multiple predetermined dose amounts comprises delivering about 10 to about 100 dose amounts.

13. The method of claim 12, wherein the predetermined dose amount is about 20 to 60 $\mu$g fentanyl halide.

14. The method of claim 13, wherein the predetermined dose amount is about 40 $\mu$g fentanyl halide.

15. The method of claim 9, wherein delivering multiple predetermined dose amounts comprises delivering about 20 to about 80 dose amounts.

16. The method of claim 9, wherein the step of delivering multiple predetermined dose amounts comprises delivering the dose amounts over at least about 6 hours.

17. The method of claim 1, wherein the analgesic drug comprises sufentanil HCl and the loading amount is at least about 4 times greater than the maximum total amount.

18. The method of claim 1, wherein the donor reservoir bas a weight on a hydrated basis of about 0.5 g to 0.8 g and is loaded with at least about 9 mg of fentanyl hydrochloride.

19. The method of claim 1, further comprising the step of preventing transient epidermal discoloration by maintaining a concentration of analgesic drug in the drug reservoir at least equal to the maximum total amount of the analgesic drug.

20. A method for transdermally delivering an active agent by electrotransport comprising the steps of:

a) providing an electrotransport delivery device having a silver anodic donor electrode, a cathodic counter electrode, and a donor reservoir containing a loading amount of the analgesic drug in electrical contact with the donor electrode, wherein the donor reservoir comprises a hydrogel containing an aqueous fentanyl salt solution that has a weight on a hydrated basis of about 0.5 g to 0.8 g, is loaded with at least about 9 mg of fentanyl hydrochloride and is substantially free of sources of halide other than the drum halide salt the device adapted to deliver a predetermined maximum total amount of analgesic drug over a period of time, the predetermined maximum total amount being at most about half the loading mount to prevent transient epidermal discoloration by silver;

b) delivering only up to the maximum total amount of the analgesic drug by delivering about 10 to about 100 predetermined dose amounts, wherein the predetermined dose amount comprises about 20 to 60 $\mu$g fentanyl halide delivered by applying a current of about 150 $\mu$A to about 240 $\mu$A for a delivery interval of about 8 to about 12 minutes;

c) maintaining the solution fentanyl concentration above 6 mg/mL in the hydrogel.

21. A method for transdermally delivering an active agent by electrotransport comprising the steps of:

a) providing an electrotransport delivery device having a silver anodic donor electrode, a cathodic counter electrode, and a donor reservoir containing a loading amount of the analgesic drug in electrical contact with the donor electrode, wherein the donor reservoir comprises a hydrogel containing an aqueous sufentanil salt solution and is substantially free of sources of halide other than ec drug halide salt, the device adapted to deliver a predetermined maximum total amount of analgesic drug over a period of time, the loading amount being at least about four times greater than the predetermined maximum total amount; and b) delivering only up to the maximum total amount of the analgesic drug by delivering about 10 to about 100 predetermined dose amounts, wherein the predetermined dose amount comprises about 4 to 5.5 $\mu$g sufentanil halide delivered by applying a current of about 150 $\mu$A to about 240 $\mu$A for a delivery interval of up to about 20 minutes;

wherein the drug reservoir prior to delivery has a loading amount of the analgesic drug that is at least about four times greater than the maximum total amount to prevent transient epidermal discoloration.

* * * * *

UNITED STATES PATENT AND TRADEMARK OFFICE
CERTIFICATE OF CORRECTION

PATENT NO.    : 6,881,208 B1
DATED         : April 19, 2005
INVENTOR(S)   : Phipps et al.

It is certified that error appears in the above-identified patent and that said Letters Patent is hereby corrected as shown below:

Column 11,
Line 47, "circuit board assembly 1" should read -- circuit board assembly 18 --.

Column 18,
Line 56, "amount being at loan about two times the predeter-" should read
-- amount being at least about two times the predeter --.

Column 19,
Line 44, "bas a weight on a hydrated basis of about 0.5 g to 0.8 g and" should read
-- has a weight on a hydrated basis of about 0.5 g to 0.8 g and --.

Column 20,
Line 10, "sources of halide other than the drum halide salt the" should read
-- sources of halide other than the drug halide salt, the --.
Line 14, "most about half the loading mount to prevent transient" should read
-- most about half the loading amount to prevent transient --.
Line 35, "other than ec drug halide salt, the device adapted to" should read
-- other than the drug halide salt, the device adapted to --.
Line 40, "b) delivering only to the maximum total amount of the" should read
-- b) delivering only to the predetermined maximum total amount of the --.

Signed and Sealed this

Twenty-seventh Day of December, 2005

JON W. DUDAS
*Director of the United States Patent and Trademark Office*